US008349345B2

(12) United States Patent
Forster et al.

(10) Patent No.: US 8,349,345 B2

(45) Date of Patent: Jan. 8, 2013

(54) FUNGICIDAL COMPOSITIONS

(75) Inventors: Birgit Forster, Stein (CH); Duncan McKenzie, Stein (CH); Jeremy Godwin, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 1229 days.

(21) Appl. No.: 12/088,030

(22) PCT Filed: Sep. 27, 2006

(86) PCT No.: PCT/EP2006/009403

§ 371 (c)(1), (2), (4) Date: Mar. 25, 2008

(87) PCT Pub. No.: WO2007/036355

PCT Pub. Date: Apr. 5, 2007

(65) Prior Publication Data

US 2008/0214397 A1 Sep. 4, 2008

(30) Foreign Application Priority Data

Sep. 29, 2005 (EP) .................................... 05021278
Nov. 28, 2005 (EP) .................................... 05025915

(51) Int. Cl.
*A01N 25/32* (2006.01)

(52) U.S. Cl. ......... 424/406; 424/405; 514/272; 514/352

(58) Field of Classification Search ........................ None
See application file for complete search history.

(56) References Cited

U.S. PATENT DOCUMENTS

| | | | | |
|---|---|---|---|---|
| 4,931,560 | A | 6/1990 | Hubele | |
| 4,997,941 | A | 3/1991 | Hubele | |
| 5,153,200 | A | 10/1992 | Hubele | |
| 5,439,926 | A * | 8/1995 | Dutzmann et al. | 514/383 |
| 5,847,005 | A | 12/1998 | Kasahara et al. | |
| 5,942,538 | A | 8/1999 | Kasahara et al. | |
| 6,346,535 | B1 * | 2/2002 | Cotter et al. | 514/269 |
| 6,586,617 | B1 | 7/2003 | Tabuchi et al. | |
| 6,682,759 | B2 | 1/2004 | Lim et al. | |
| 6,710,062 | B1 | 3/2004 | Hayashi et al. | |
| 6,812,229 | B1 | 11/2004 | Ozaki et al. | |
| 2003/0050194 | A1 * | 3/2003 | Hopkinson et al. | 504/363 |
| 2003/0063834 | A1 | 4/2003 | Godbout et al. | |
| 2003/0072802 | A1 | 4/2003 | Cutler | |
| 2008/0020999 | A1 * | 1/2008 | Klapproth et al. | 514/63 |

FOREIGN PATENT DOCUMENTS

| | | |
|---|---|---|
| EP | 0310550 | 4/1989 |
| EP | 0353191 | 1/1990 |
| EP | 1035122 | 9/2000 |
| JP | 2000319270 | 11/2000 |
| KR | 2003-0066351 | 8/2003 |
| WO | 9522818 | 12/1995 |
| WO | 9619442 | 6/1996 |
| WO | 9846607 | 10/1998 |
| WO | 0065913 | 11/2000 |
| WO | 0110825 A1 | 2/2001 |
| WO | 02062759 | 8/2002 |
| WO | 03/020200 A2 | 3/2003 |

OTHER PUBLICATIONS

Colby, S. R., "Calculating Synergistic and Antagonistic Responses of Herbicide Combination", Weeds, vol. 15, pp. 20-22, 1967.
"The Pesticide Manual" (The Pesticide Manual—A Word compendium; Thirtheenth Edition; Editor: C.D.S. Tomlin; The British Corp Protection Council), 2003.

* cited by examiner

*Primary Examiner* — Neil Levy
(74) *Attorney, Agent, or Firm* — R. Kody Jones

(57) ABSTRACT

A composition for control of diseases on useful plants or on propagation material thereof caused by phytopathogens, that, in addition to customary inert formulation adjuvants, comprises as active ingredient a mixture of component (A) and a synergistically effective amount of component (B), wherein component (A) is Cyprodinil; and component (B) a compound selected from compounds known for their fungicidal activity, is particularly effective in controlling or preventing fungal diseases of useful plants.

10 Claims, No Drawings

FUNGICIDAL COMPOSITIONS

This application is a 371 of International Application No. PCT/EP2006/009403 filed Sep. 27, 2006, which claims priority to EP 05021278.6 filed Sep. 29, 2005 and EP 05025915.9 filed Nov. 28, 2005, the contents of which are incorporated herein by reference.

The present invention relates to novel fungicidal compositions for the treatment of diseases of useful plants caused by phytopathogens, especially by phytopathogenic fungi, and to a method of controlling diseases on useful plants.

EP-0-310-550 discloses Cyprodinil ((4-cyclopropyl-6-methyl-pyrimidin-2-yl)-phenyl-amine), a fungicide which is effective against a number of diseases caused by ascomycetes or deuteromycetes. On the other hand various fungicidal compounds of different chemical classes are widely known as plant fungicides for application in various crops of cultivated plants. However, crop tolerance and activity against phytopathogenic plant fungi do not always satisfy the needs of agricultural practice in many incidents and aspects.

Out of the above-mentioned needs of agricultural practice for increased crop tolerance and/or increased activity against phytopathogenic plant fungi, there is therefore proposed in accordance with the present invention a novel synergistic composition for control of diseases on useful plants or on propagation material thereof caused by phytopathogens, that in addition to customary inert formulation adjuvants, comprises as active ingredient a mixture of component (A) and a synergistically effective amount of component (B), wherein component (A) is Cyprodinil (208); and component (B) is a compound selected from Dodine (289); Chlorothalonil (142); Folpet (400); Prothioconazole (685); Boscalid (88); Proquinazid (682); Dithianon (279); Fluazinam (363); Ipconazole (468); Metrafenone; a compound of formula A-1

(A-1)

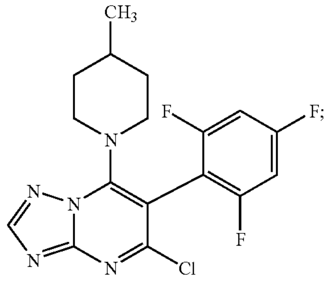

a compound of formula A-2

(A-2)

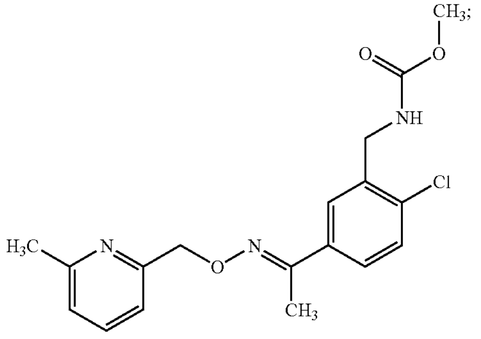

a compound of formula A-3

(A-3)

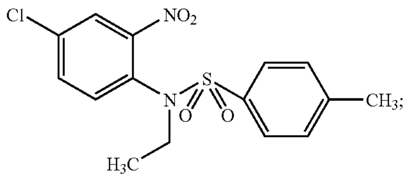

a compound of formula A-4

(A-4)

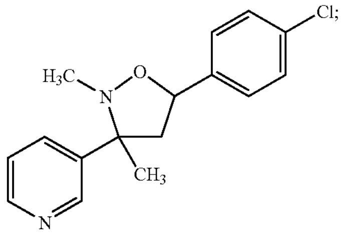

a compound of formula A-5

(A-5)

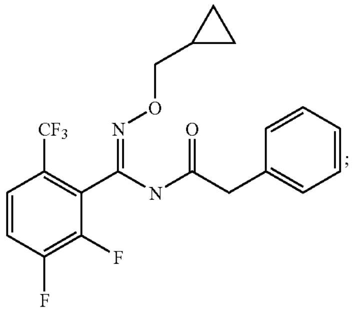

and a compound of formula A-6

(A-6)

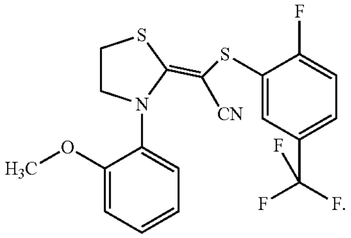

It has now been found, surprisingly, that the active ingredient mixture according to the invention not only brings about the additive enhancement of the spectrum of action with respect to the phytopathogen to be controlled that was in principle to be expected but achieves a synergistic effect which extends the range of action of the component (A) and of the component (B) in two ways. Firstly, the rates of application of the component (A) and of the component (B) are lowered whilst the action remains equally good. Secondly, the active ingredient mixture still achieves a high degree of phytopathogen control even where the two individual components have become totally ineffective in such a low application rate range. This allows, on the one hand, a substantial broadening of the spectrum of phytopathogens that can be controlled and, on the other hand, increased safety in use.

However, besides the actual synergistic action with respect to fungicidal activity, the pesticidal compositions according to the invention can also have further surprising advantageous properties which can also be described, in a wider sense, as synergistic activity. Examples of such advantageous properties that may be mentioned are: a broadening of the spectrum of fungicidal activity to other phytopathogens, for example to resistant strains; a reduction in the rate of application of the active ingredients; synergistic activity against animal pests, such as insects or representatives of the order Acarina; a broadening of the spectrum of pesticidal activity to other animal pests, for example to resistant animal pests; adequate pest control with the aid of the compositions according to the invention, even at a rate of application at which the individual compounds are totally ineffective; advantageous behaviour during formulation and/or upon application, for example upon grinding, sieving, emulsifying, dissolving or dispensing; increased storage stability; improved stability to light; more advantageuos degradability; improved toxicological and/or ecotoxicological behaviour; or improved characteristics of the useful plants including: emergence, crop yields, more developed root system, tillering increase, increase in plant height, bigger leaf blade, less dead basal leaves, stronger tillers, greener leaf colour, less fertilizers needed, less seeds needed, more productive tillers, earlier flowering, early grain maturity, less plant verse (lodging), increased shoot growth, improved plant vigor, and early germination.

A further aspect of the instant invention is a method of controlling diseases on useful plants or on propagation material thereof caused by phytopathogens, which comprises applying to the useful plants, the locus thereof or propagation material thereof a composition according to the invention.

Cyprodinil and some components B) are described in "The Pesticide Manual" [The Pesticide Manual—A World Compendium; Thirteenth Edition; Editor: C. D. S. Tomlin; The British Crop Protection Council]. Cyprodinil and those components B) are described therein under the entry number given in round brackets hereinabove for the particular component A) or B); for example, the compound "Chlorothalonil" is described under entry number (142). All of those components A) or B) are referred to hereinabove by a so-called "common name".

The following components B) are registered under a CAS-Reg. No. http://www/: Metrafenone (CAS 220899-03-6); the compound of formula A-1 is described in WO 98/46607 and is registered under CAS-214706-53-3; the compound of formula A-2 is described in WO 02/062759 and in WO 01/010825, is registered under CAS-Reg. No. http://www/: 325156-49-8 and is also known as Pyribencarb; the compound of formula A-3 is described in WO 00/065913 and is registered under CAS-304911-98-6; the compound of formula A-4 is described in EP-1-035-122 and is registered under CAS-291771-99-8 and CAS-291771-83-0; the compound of formula A-5 is described in WO 96/19442 and is also known as Cyflufenamid (CAS-180409-60-3); and the compound of formula A-6 is described in JP-2000-319270 and is registered under CAS-304900-25-2.

According to the instant invention component (A) and/or component (B) can be used to prepare the compositions of the invention either in the free form or as a salt or metal complex thereof.

An example of a compound, that can be used to prepare the compositions of the invention either in the free form or as a salt or metal complex thereof, is cyprodinil.

Of the acids that can be used for the preparation of salts of cyprodinil, the following may be mentioned: hydrohalic acids, such as hydrofluoric acid, hydrochloric acid, hydrobromic acid or hydriodic acid; sulfuric acid, phosphoric acid, nitric acid, and organic acids, such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid, 2-acetoxybenzoic acid and 1,2-naphthalene-disulfonic acid.

Metal complexes consist of the underlying organic molecule and an inorganic or organic metal salt, for example a halide, nitrate, sulfate, phosphate, acetate, trifluoroacetate, trichloroacetate, propionate, tartrate, sulfonate, salicylate, benzoate, etc., of an element of main group II, such as calcium and magnesium, and of main groups III and IV, such as aluminium, tin or lead, and of subgroups I to VIII, such as chromium, manganese, iron, cobalt, nickel, copper, zinc, etc. Preference is given to the subgroup elements of the 4th period. The metals may have any of the different valencies in which they occur. The metal complexes can be mono- or poly-nuclear, i.e. they can contain one or more organic molecule components as ligands.

In one embodiment of the invention, cyprodinil is used in the free form to prepare the compositions of the invention.

In one embodiment of the invention, the compound of component (B) is used in the free form to prepare the compositions of the invention.

Throughout this document the expression "composition" stands for the various mixtures or combinations of components A) and B), for example in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the components A) and B) is not essential for working the present invention.

The compositions according to the invention may also comprise more than one of the active components B), if, for example, a broadening of the spectrum of disease control is desired. For instance, it may be advantageous in the agricultural practice to combine two or three components B) with Cyprodinil. Said compositions may comprise also one or more further agrochemical active ingredients, such as herbicides, fungicides, insecticides, nematocides or plant-growth regulators.

A preferred embodiment of the present invention is represented by those compositions, wherein component B) is selected from Boscalid; Proquinazid; Dodine; Fluazinam; Ipconazole; a compound of formula A-2; a compound of formula A-3; a compound of formula A-4 and a compound of formula A-6.

Another preferred embodiment of the present invention is represented by those compositions, wherein component B) is selected from Boscalid; Dodine; a compound of formula A-2 and a compound of formula A-3.

Another preferred embodiment of the present invention is represented by those compositions, wherein component B) is selected from Boscalid; Dodine; Fluazinam and a compound of formula A-2.

Another preferred embodiment of the present invention is represented by those compositions, wherein component B) is selected from Boscalid; Dodine and a compound of formula A-2.

Another preferred embodiment of the present invention is represented by those compositions, wherein component B) is Chlorothalonil.

Another preferred embodiment of the present invention is represented by those compositions, wherein component B) is Folpet.

Another preferred embodiment of the present invention is represented by those compositions, wherein component B) is Prothioconazole.

Another preferred embodiment of the present invention is represented by those compositions, wherein component B) is Boscalid.

Another preferred embodiment of the present invention is represented by those compositions, wherein component B) is Proquinazid.

Another preferred embodiment of the present invention is represented by those compositions, wherein component B) is Dodine.

Another preferred embodiment of the present invention is represented by those compositions, wherein component B) is Dithianon.

Another preferred embodiment of the present invention is represented by those compositions, wherein component B) is Fluazinam.

Another preferred embodiment of the present invention is represented by those compositions, wherein component B) is Ipconazole.

Another preferred embodiment of the present invention is represented by those compositions, wherein component B) is Metrafenone.

Another preferred embodiment of the present invention is represented by those compositions, wherein component B) is a compound of formula A-1.

Another preferred embodiment of the present invention is represented by those compositions, wherein component B) is a compound of formula A-2.

Another preferred embodiment of the present invention is represented by those compositions, wherein component B) is a compound of formula A-3.

Another preferred embodiment of the present invention is represented by those compositions, wherein component B) is a compound of formula A-4.

Another preferred embodiment of the present invention is represented by those compositions, wherein component B) is a compound of formula A-5.

Another preferred embodiment of the present invention is represented by those compositions, wherein component B) is a compound of formula A-6.

The compositions according to the invention are effective against harmful microorganisms, such as microorganisms, that cause plant diseases, in particular against phytopathogenic fungi and bacteria.

The compositions according to the invention are effective especially against phytopathogenic fungi belonging to the following classes: Ascomycetes (e.g. *Venturia, Podosphaera, Erysiphe, Monilinia, Mycosphaerella, Uncinula, Botrytis, Helminthosporium, Fusarium, Septoria, Cercospora, Rhynchosporium, Pyricularia* and *Pseudocercosporella*); Basidiomycetes (e.g. the genus *Hemileia, Rhizoctonia, Phakopsora, Puccinia, Ustilago, Tilletia*); Fungi imperfecti (also known as Deuteromycetes; e.g. *Alternaria*).

According to the invention "useful plants" typically comprise the following species of plants: grape vines; cereals, such as wheat, barley, rye or oats; beet, such as sugar beet or fodder beet; fruits, such as pomes, stone fruits or soft fruits, for example apples, pears, plums, peaches, almonds, cherries, strawberries, raspberries or blackberries; leguminous plants, such as beans, lentils, peas or soybeans; oil plants, such as rape, mustard, poppy, olives, sunflowers, coconut, castor oil plants, cocoa beans or groundnuts; cucumber plants, such as marrows, cucumbers or melons; fibre plants, such as cotton, flax, hemp or jute; citrus fruit, such as oranges, lemons, grapefruit or mandarins; vegetables, such as spinach, lettuce, asparagus, cabbages, carrots, onions, tomatoes, potatoes, cucurbits or paprika; lauraceae, such as avocados, cinnamon or camphor; maize; tobacco; nuts; coffee; sugar cane; tea; vines; hops; durian; bananas; natural rubber plants; turf or ornamentals, such as flowers, shrubs, broad-leaved trees or evergreens, for example conifers. This list does not represent any limitation.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Useful plants of elevated interest in connection with present invention are cereals; soybean; rice; oil seed rape; pome fruits; stone fruits; peanuts; coffee; tea; strawberries; turf; vines and vegetables, such as tomatoes, potatoes, cucurbits and lettuce.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of a plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion.

Preferably "plant propagation material" is understood to denote seeds.

A further aspect of the instant invention is a method of protecting natural substances of plant and/or animal origin, which have been taken from the natural life cycle, and/or their processed forms against attack of fungi, which comprises applying to said natural substances of plant and/or animal origin or their processed forms a compositions according to the invention.

According to the instant invention, the term "natural substances of plant origin, which have been taken from the natural life cycle" denotes plants or parts thereof which have been harvested from the natural life cycle and which are in the freshly harvested form. Examples of such natural substances of plant origin are stalks, leafs, tubers, seeds, fruits or grains. According to the instant invention, the term "processed form of a natural substance of plant origin" is understood to denote a form of a natural substance of plant origin that is the result of a modification process. Such modification processes can be used to transform the natural substance of plant origin in a more storable form of such a substance (a storage good). Examples of such modification processes are pre-drying, moistening, crushing, comminuting, grounding, compressing or roasting. Also falling under the definition of a processed form of a natural substance of plant origin is timber, whether in the form of crude timber, such as construction timber, electricity pylons and barriers, or in the form of finished articles, such as furniture or objects made from wood.

According to the instant invention, the term "natural substances of animal origin, which have been taken from the natural life cycle and/or their processed forms" is understood to denote material of animal origin such as skin, hides, leather, furs, hairs and the like.

The compositions according to the invention can prevent disadvantageous effects such as decay, discoloration or mold.

A preferred embodiment is a method of protecting natural substances of plant origin, which have been taken from the natural life cycle, and/or their processed forms against attack of fungi, which comprises applying to said natural substances of plant and/or animal origin or their processed forms a compositions according to the invention.

A further preferred embodiment is a method of protecting fruits, preferably pomes, stone fruits, soft fruits and citrus fruits, which have been taken from the natural life cycle, and/or their processed forms, which comprises applying to said fruits and/or their processed forms a compositions according to the invention.

The compositions according to the invention may also be used in the field of protecting industrial material against attack of fungi. According to the instant invention, the term "industrial material" denotes non-live material which have been prepared for use in industry. For example, industrial materials which are intended to be protected against attack of fungi can be glues, sizes, paper, board, textiles, carpets, leather, wood, constructions, paints, plastic articles, cooling lubricants, aquaeous hydraulic fluids and other materials which can be infested with, or decomposed by, microorganisms. Cooling and heating systems, ventilation and air conditioning systems and parts of production plants, for example cooling-water circuits, which may be impaired by multiplication of microorganisms may also be mentioned from amongst the materials to be protected. The compositions according to the invention can prevent disadvantageous effects such as decay, discoloration or mold.

The compositions according to the invention may also be used in the field of protecting technical material against attack of fungi. According to the instant invention, the term "technical material" includes paper; carpets; constructions; cooling and heating systems; ventilation and air conditioning systems and the like. The compositions according to the invention can prevent disadvantageous effects such as decay, discoloration or mold.

The compositions according to the invention are particularly effective against powdery mildews; rusts; leafspot species; early blights and molds; especially against *Septoria, Puccinia, Erysiphe, Rhynchosporium, Pyrenophora* and *Tapesia* in cereals; *Phakopsora* in soybeans; *Hemileia* in coffee; *Phragmidium* in roses; *Alternaria* in potatoes, tomatoes and cucurbits; *Sclerotinia* in turf, vegetables, sunflower and oil seed rape; black rot, red fire, powdery mildew, grey mold and dead arm disease in vine; *Botrytis cinerea* in fruits; *Venturia* and *Monilinia* spp. in fruits and *Penicillium* spp. in fruits.

The compositions according to the invention are furthermore particularly effective against seedborne and soilborne diseases, such as *Alternaria* spp., *Ascochyta* spp., *Botrytis cinerea, Cercospora* spp., *Claviceps purpurea, Cochliobolus sativus, Colletotrichum* spp., *Epicoccum* spp., *Fusarium graminearum, Fusarium moniliforme, Fusarium oxysporum, Fusarium proliferatum, Fusarium solani, Fusarium subglutinans, Gäumannomyces graminis, Helminthosporium* spp., *Microdochium nivale, Phoma* spp., *Pyrenophora graminea, Pyricularia oryzae, Rhizoctonia solani, Rhizoctonia cerealis, Sclerotinia* spp., *Septoria* spp., *Sphacelotheca reilliana, Tilletia* spp., *Typhula incarnata, Urocystis occulta, Ustilago* spp. or *Verticillium* spp.; in particular against pathogens of cereals, such as wheat, barley, rye or oats; maize; rice; cotton; soybean; turf; sugarbeet; oil seed rape; potatoes; pulse crops, such as peas, lentils or chickpea; and sunflower.

The compositions according to the invention are furthermore particularly effective against post harvest diseases such as *Botrytis cinerea, Colletotrichum musae, Curvularia lunata, Fusarium semitecum, Geotrichum candidum, Monilinia fructicola, Monilinia fructigena, Monilinia laxa, Mucor piriformis, Penicilium italicum, Penicilium solitum, Penicillium digitatum* or *Penicillium expansum* in particular against pathogens of fruits, such as pomefruits, for example apples and pears, stone fruits, for example peaches and plums, citrus, melons, papaya, kiwi, mango, berries, for example strawberries, avocados, pomegranates and bananas, and nuts.

The amount of a composition according to the invention to be applied, will depend on various factors, such as the compounds employed; the subject of the treatment, such as, for example plants, soil or seeds; the type of treatment, such as, for example spraying, dusting or seed dressing; the purpose of the treatment, such as, for example prophylactic or therapeutic; the type of fungi to be controlled or the application time.

It has been found that the use of components B) in combination with Cyprodinil surprisingly and substantially enhance the effectiveness of the latter against fungi, and vice versa. Additionally, the method of the invention is effective against a wider spectrum of such fungi that can be combated with the active ingredients of this method, when used solely.

The weight ratio of A):B) is so selected as to give a synergistic activity. In general the weight ratio of A):B) is between 2000:1 and 1:1000, preferably between 100:1 and 1:100, more preferably between 20:1 and 1:50.

The synergistic activity of the compositions according to the invention is apparent from the fact that the fungicidal activity of the composition of A)+B) is greater than the sum of the fungicidal activities of A) and B).

The method of the invention comprises applying to the useful plants, the locus thereof or propagation material thereof in admixture or separately, a composition according to the invention.

Some of said compositions according to the invention have a systemic action and can be used as foliar, soil and seed treatment fungicides.

With the compositions according to the invention it is possible to inhibit or destroy the phytopathogenic microorganisms which occur in plants or in parts of plants (fruit, blossoms, leaves, stems, tubers, roots) in different useful plants, while at the same time the parts of plants which grow later are also protected from attack by phytopathogenic microorganisms.

The compositions according to the invention are of particular interest for controlling a large number of fungi in various useful plants or their seeds, especially in field crops such as potatoes, tobacco and sugarbeets, and wheat, rye, barley, oats, rice, maize, lawns, cotton, soybeans, oil seed rape, pulse crops, sunflower, coffee, sugarcane, fruit and ornamentals in horticulture and viticulture, in vegetables such as cucumbers, beans and cucurbits.

The compositions according to the invention are applied by treating the fungi, the useful plants, the locus thereof, the propagation material thereof, the natural substances of plant and/or animal origin, which have been taken from the natural life cycle, and/or their processed forms, or the industrial materials threatened by fungus attack with a compositions according to the invention.

The compositions according to the invention may be applied before or after infection of the useful plants, the propagation material thereof, the natural substances of plant and/or animal origin, which have been taken from the natural life cycle, and/or their processed forms, or the industrial materials by the fungi.

The compositions according to the invention are particularly useful for controlling the following plant diseases:

*Alternaria* species in fruit and vegetables, such as *Alternaria solani* on tomatoes,
*Ascochyta* species in pulse crops,
*Botrytis cinerea* in strawberries, tomatoes, sunflower, pulse crops, vegetables and grapes,
*Cercospora arachidicola* in peanuts,
*Cochliobolus sativus* in cereals,
*Colletotrichum* species in pulse crops,
*Erysiphe* species in cereals, such as *Erysiphe graminis* f sp *hordei* on barley or *Erysiphe graminis* f sp *tritici* on wheat,
*Erysiphe cichoracearum* and *Sphaerotheca fuliginea* in cucurbits,
*Fusarium* species in cereals and maize,
*Gäumannomyces graminis* in cereals and lawns,
*Helminthosporium* species in maize, rice and potatoes,
*Hemileia vastatrix* on coffee,
*Leptoshaeria nodorum* on wheat,
*Microdochium* species in wheat and rye,
*Phakopsora* species in soybean,
*Podoshphaera leucotricha* on apple,
*Puccinia* species in cereals, broadleaf crops and perrenial plants,
*Pseudocercosporella* species in cereals,
*Phragmidium mucronatum* in roses,
*Podosphaera* species in fruits,
*Pyrenophora* species in barley,
*Pyricularia oryzae* in rice,
*Ramularia collo-cygni* in barley,
*Rhizoctonia* species in cotton, soybean, cereals, maize, potatoes, rice and lawns,
*Rhynchosporium secalis* in barley and rye,
*Sclerotinia* species in lawns, lettuce, vegetables and oil seed rape,
*Septoria* species in cereals, soybean and vegetables, such as *Septoria tritici* on wheat,
*Sphacelotheca reilliana* in maize,
*Tilletia* species in cereals,
*Uncinula necator, Guignardia bidwellii* and *Phomopsis viticola* in vines,
*Urocystis occulta* in rye,
*Ustilago* species in cereals and maize,
*Venturia* species in fruits, such as *Venturia inaequalis* on apple,
*Monilinia* species on fruits,
*Penicillium* species on citrus and apples.

When applied to the useful plants Cyprodinil is applied at a rate of 5 to 2000 g a.i./ha, particularly 10 to 1000 g a.i./ha, e.g. 15, 25, 50, 300, 400, 500, 600 or 750 g a.i./ha, in association with 1 to 5000 g a.i./ha, particularly 2 to 2000 g a.i./ha, e.g. 100, 250, 500, 800, 1000, 1500 g a.i./ha of a compound of component B), depending on the class of chemical employed as component B).

In agricultural practice the application rates of the compositions according to the invention depend on the type of effect desired, and typically range from 20 to 4000 g of total composition per hectare.

When the compositions according to the invention are used for treating seed, rates of 0.001 to 10 g of Cyprodinil per kg of seed, preferably from 0.01 to 1 g per kg of seed, and 0.001 to 50 g of a compound of component B), per kg of seed, preferably from 0.01 to 10 g per kg of seed, are generally sufficient.

The composition of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g. by mixing the active ingredients with appropriate inert formulation adjuvants (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the compositions according to the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula I together with a compound of component B), and optionally other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

The Examples which follow serve to illustrate the invention, "active ingredient" denoting a mixture of cyprodinil and a compound of component B) in a specific mixing ratio.

FORMULATION EXAMPLES

| Wettable powders | a) | b) | c) |
|---|---|---|---|
| active ingredient [A):B) = 1:3(a), 1:2(b), 1:1(c)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredient [A):B) = 1:3(a), 1:2(b), 1:1(c)] | 25% | 50% | 75% |
| light mineral oil | 5% | 5% | 5% |
| highly dispersed silicic acid | 5% | 5% | — |
| Kaolin | 65% | 40% | — |
| Talcum | — | | 20 |

The active ingredient is thoroughly mixed with the adjuvants and the mixture is thoroughly ground in a suitable mill, affording powders that can be used directly for seed treatment.

Emulsifiable Concentrate

| | |
|---|---|
| active ingredient (A):B) = 1:6) | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredient [A):B) = 1:6(a), 1:2(b), 1:10(c)] | 5% | 6% | 4% |
| Talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

Extruder Granules

| | |
|---|---|
| Active ingredient (A):B) = 2:1) | 15% |
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

Coated Granules

| | |
|---|---|
| Active ingredient (A):B) = 1:10) | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

Suspension Concentrate

| | |
|---|---|
| active ingredient (A):B) = 1:8) | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| | |
|---|---|
| active ingredient (A):B) = 1:8) | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of a combination of cyprodinil and a compound of component B), or of each of these compounds separately, are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8-15 microns.

The resulting formulation is applied to seeds as an aqueous suspension in an apparatus suitable for that purpose.

A further aspect of the instant invention is a method of controlling diseases on useful plants caused by phytopathogens, which comprises applying to the useful plants or the locus thereof a composition according to the invention.

A further aspect of the instant invention is a method of controlling diseases on useful plants caused by phytopathogens, which comprises applying to the useful plants a composition according to the invention.

A further aspect of the instant invention is a method of controlling diseases on cereal plants caused by phytopathogens, which comprises applying to the cereal plants or to the locus thereof a composition according to the invention; preferred cereal plants are wheat or barley.

Within this embodiment, further preferred is a method of controlling diseases on wheat plants caused by phytopathogens, which comprises applying to the wheat plants or to the locus thereof a composition according to the invention, wherein the disease is a disease selected from the group consisting of *Blumeria graminis* (*Erysiphe graminis*), *Pseudocercosporella herpotrichoides, Puccinia recondita, Puccinia striiformis, Pyrenophora tritici-repentis, Septoria tritici* and *Tapesia* spp. Within this embodiment, further preferred is a method of controlling *Tapesia* spp. on wheat plants, which comprises applying to the wheat plants or to the locus thereof a composition according to the invention. Within this embodiment, further preferred is a method of controlling *Blumeria graminis* f. sp. *tritici* on wheat plants, which comprises applying to the wheat plants or to the locus thereof a composition according to the invention.

Further preferred is a method of controlling diseases on barley plants caused by phytopathogens, which comprises applying to the barley plants or to the locus thereof a composition according to the invention, wherein the disease is a disease selected from the group consisting of *Blumeria graminis* (*Erysiphe graminis*), *Puccinia hordei, Puccinia striiformis, Puccinia graminis, Pyrenophora teres, Ramularia collo-cygni* and *Rhynchosporium secalis*; preferred is a method, wherein the disease is a disease selected from the group consisting of *Pyrenophora teres, Ramularia collo-cygni* and *Rhynchosporium secalis.*

Within this embodiment, further preferred is a method of controlling *Ramularia collo-cygni* on barley plants, which comprises applying to the barley plants or to the locus thereof a composition according to the invention.

A further aspect of the instant invention is a method of controlling diseases on fruit plants or vegetable plants caused by phytopathogens, which comprises applying to the fruit plants or vegetable plants or to the locus thereof a composition according to the invention; preferred fruit plants are citrus, apple, pear, strawberry or banana; preferred vegetable plants are tomato; potato; cucurbit, such as cucumber or melon; leafy vegetables, such as lettuce, spinach or celery; *brassica*, such as cabbage, cauliflower, oilseed rape, broccoli or brussels sprouts; *allium*, such as onion or leek; root crops, such as sugar beet, carrots or parsnips; or legumes, such as peas or beans.

Within this embodiment, further preferred is a method of controlling diseases on fruit plants or vegetable plants caused by phytopathogens, which comprises applying to the fruit plants or vegetable plants or to the locus thereof a composition according to the invention, wherein the disease is a disease selected from the group consisting of *Alternaria* spp, *Diaporthe* spp, *Mycosphaerella* spp, *Sphaerotheca* spp, *Sclerotinia* spp, *Botrytis* spp, *Phoma* spp. *Venturia* spp. and *Colletotrichum* spp; preferred is a method, wherein the disease is *Alternaria* spp.

Further preferred is a method of controlling diseases on fruit plants caused by phytopathogens, which comprises applying to the fruit plants or to the locus thereof a composition according to the invention, wherein the fruit plant is selected from citrus, apple, pear, strawberry and banana, and wherein the disease is selected from *Alternaria* spp, *Diaporthe* spp, *Mycosphaerella* spp, *Sphaerotheca* spp, *Sclerotinia* spp, *Botrytis* spp, *Phoma* spp. *Venturia* spp. and *Colletotrichum* spp; preferred is a method, wherein the disease is *Alternaria* spp.; in a further preferred embodiment, the disease is *Botrytis cinerea*. Further preferred is a method of controlling diseases on vegetable plants caused by phytopathogens, which comprises applying to the vegetable plants or to the locus thereof a composition according to the invention, wherein the vegetable plant is selected from tomato, potato, cucumber, lettuce, spinach, celery, cabbage, cauliflower, oilseed rape, broccoli, brussels sprouts, onion, leek, sugar beet, carrots, parsnips, peas and beans, and wherein the disease is selected from *Alternaria* spp, *Diaporthe* spp, *Mycosphaerella* spp, *Sphaerotheca* spp, *Sclerotinia* spp, *Botrytis* spp, *Phoma* spp. *Venturia* spp. and *Colletotrichum* spp; preferred is a method, wherein the disease is *Alternaria* spp.; in a further preferred embodiment, the disease is *Botrytis cinerea.*

A further aspect of the instant invention is a method of controlling diseases on grape plants caused by phytopathogens, which comprises applying to the grape plants or to the locus thereof a composition according to the invention.

Within this embodiment, further preferred is a method of controlling diseases on grape plants caused by phytopathogens, which comprises applying to the grape plants or to the locus thereof a composition according to the invention, wherein the disease is selected from the group consisting of *Botrytis cinerea, Uncinula necator, Guignardia bidwellii* and *Plasmopara viticola*; preferred is a method, wherein the disease is *Botrytis cinerea.*

Furthermore preferred is a method of controlling *Botrytis* spp, preferably *Botrytis cinerea*, on useful plants, which comprises applying to the useful plants or to the locus thereof a composition according to the invention, wherein the active ingredient comprises at least a mixture of Cyprodinil and Boscalid.

Furthermore preferred is a method of controlling *Botrytis* spp, preferably *Botrytis cinerea*, on useful plants, which comprises applying to the useful plants or to the locus thereof a composition according to the invention, wherein the active ingredient comprises at least a mixture of Cyprodinil and a compound of formula A-2.

Furthermore preferred is a method of controlling *Botrytis* spp, preferably *Botrytis cinerea*, on useful plants, which comprises applying to the useful plants or to the locus thereof a composition according to the invention, wherein the active ingredient comprises at least a mixture of Cyprodinil and a compound of formula A-4.

Furthermore preferred is a method of controlling *Venturia* spp on useful plants, which comprises applying to the useful plants or to the locus thereof a composition according to the invention, wherein the active ingredient comprises at least a mixture of Cyprodinil and Dodine.

Furthermore preferred is a method of controlling *Alternaria* spp on useful plants, which comprises applying to the useful plants or to the locus thereof a composition according to the invention, wherein the active ingredient comprises at least a mixture of Cyprodinil and a compound of formula A-3.

Furthermore preferred is a method of controlling *Fusarium* spp on useful plants, which comprises applying to the useful plants or to the locus thereof a composition according to the invention, wherein the active ingredient comprises at least a mixture of Cyprodinil and Ipconazole.

BIOLOGICAL EXAMPLES

A synergistic effect exists whenever the action of an active ingredient combination is greater than the sum of the actions of the individual components.

The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20-22; 1967):

ppm=milligrams of active ingredient (=a.i.) per liter of spray mixture

X=% action by active ingredient A) using p ppm of active ingredient

Y=% action by active ingredient B) using q ppm of active ingredient.

According to COLBY, the expected (additive) action of active ingredients A)+B) using p+q ppm of active ingredient is $$E = X + Y - \frac{X \cdot Y}{100}$$

If the action actually observed (O) is greater than the expected action (E), then the action of the combination is super-additive, i.e. there is a synergistic effect.

Example B-1

Action Against *Botrytis cinerea* (Causal Fungus of Gray Mould)

a) Fungal Growth Assay

Conidia of the fungus from cryogenic storage are directly mixed into nutrient broth (PDB potato dextrose broth). After placing a (DMSO) solution of the test compounds into a microtiter plate (96-well format) the nutrient broth containing the fungal spores is added. The test plates are incubated at 24 C and the inhibition of growth is determined photometrically after 3 days. The fungicide interactions in the combinations are calculated according to the COLBY method. The data generated in this experiment indicate synergy between cyprodinil and dodine and cyprodinil and pyribencarb when used in mixture with one another.

Control of *Botrytis cinerea*
Dosage in mg active ingredient/liter final medium

| Cyprodinil (ppm ai) [mg/L] | | Observed control in % (% $C_{obs}$) observed | Expected control in % (% $C_{exp}$) expected | Synergistic benefit in % control % $C_{obs}$ − % $C_{exp}$ difference |
|---|---|---|---|---|
| | Dodine (ppm ai) [mg/L] | | | |
| 0.5 | — | 26.7 | — | — |
| 1 | — | 38.2 | — | — |
| 2 | — | 50.5 | — | — |
| 4 | — | 40.1 | — | — |
| 8 | — | 51.8 | — | — |
| — | 4 | 0 | — | — |
| — | 8 | 0 | — | — |
| — | 16 | 36.3 | — | — |
| 8 | 8 | 82.6 | 51.8 | +30.8 |
| 4 | 4 | 53.1 | 40.1 | +13.0 |
| 8 | 16 | 98.0 | 69.3 | +28.7 |
| 4 | 16 | 97.5 | 61.8 | +35.7 |
| 2 | 16 | 81.5 | 68.5 | +13.0 |
| 1 | 8 | 54.5 | 38.2 | +16.3 |
| 0.5 | 4 | 43.5 | 26.7 | +16.8 |
| | Pyribencarb (ppm ai) [mg/L] | | | |
| 0.125 | — | 16.7 | — | — |
| 0.25 | — | 22.6 | — | — |
| 0.5 | — | 21.4 | — | — |
| 1 | — | 25.7 | — | — |
| 2 | — | 23.2 | — | — |
| 4 | — | 37.1 | — | — |
| — | 0.008 | 0.4 | — | — |
| — | 0.016 | 0 | — | — |
| — | 0.031 | 3.3 | — | — |
| — | 0.063 | 2.6 | — | — |
| — | 0.125 | 16.4 | — | — |
| 4 | 0.063 | 51.5 | 38.8 | +12.7 |
| 2 | 0.031 | 39.2 | 25.7 | +13.5 |
| 4 | 0.125 | 61.3 | 47.4 | +13.9 |
| 2 | 0.063 | 43.9 | 25.2 | +18.7 |
| 1 | 0.031 | 32.0 | 28.1 | +3.9 |
| 0.5 | 0.016 | 32.6 | 21.4 | +11.2 |
| 0.25 | 0.016 | 33.6 | 22.6 | +11.0 |
| 0.125 | 0.008 | 32.2 | 17.0 | +15.2 |

b) Protective Treatment of Bean Leaf Pieces

Bean leaf disks are placed on agar in multiwell plates (24-well format) and sprayed with test solutions. After drying, the leaf disks are inoculated with a spore suspension of the fungus. After appropriate incubation the activity of a compound is assessed 4 days after inoculation as preventive fungicidal activity. The fungicide interactions in the combinations are calculated according to the COLBY method.

c) Protective Treatment of Whole Grape Plants 5 week old grape seedlings cv. Gutedel are treated with the formulated test compound in a spray chamber. Two days after application, the grape plants are inoculated by spraying a spore suspension ($1\times10^6$ conidia/ml) on the test plants. After an incubation period of 4 days at 21° C. and 95% relative humidity in a greenhouse the percentage leaf area covered by disease is assessed. The fungicide interactions in the combinations are calculated according to the COLBY method.

d) Protective Treatment of Whole Tomato Plants 4 week old tomato plants cv. Roter Gnom are treated with the formulated test compound in a spray chamber. Two days after application, the tomato plants are inoculated by spraying a spore suspension ($1\times10^5$ conidia/ml) on the test plants. After an incubation period of 4 days at 20° C. and 95% relative humidity in a growth chamber the percentage leaf area covered by disease is assessed. The fungicide interactions in the combinations are calculated according to the COLBY method.

Example B-2

Action Against *Pyrenophora teres* (Causal Fungus of Net Blotch on Barley)

a) Fungal Growth Assay

Conidia of the fungus from cryogenic storage are directly mixed into nutrient broth (PDB potato dextrose broth). After placing a (DMSO) solution of the test compounds into a microtiter plate (96-well format) the nutrient broth containing the fungal spores is added. The test plates are incubated at 24° C. and the inhibition of growth is determined photometrically after 2 days. The fungicide interactions in the combinations are calculated according to the COLBY method. The data generated in this experiment indicate synergy between cyprodinil and pyribencarb when used in mixture with one another.

Control of *Pyrenophora teres*
Dosage in mg active ingredient/liter final medium

| Cyprodinil (ppm ai) [mg/L] | Pyribencarb (ppm ai) [mg/L] | Observed control in % (% $C_{obs}$) observed | Expected control in % (% $C_{exp}$) expected | Synergistic benefit in % control % $C_{obs}$ − % $C_{exp}$ difference |
|---|---|---|---|---|
| 0.25 | — | 52.0 | — | — |
| 0.5 | — | 59.0 | — | — |
| — | 0.004 | 0 | — | — |
| — | 0.008 | 0 | — | — |
| — | 0.016 | 0 | — | — |
| — | 0.031 | 0 | — | — |
| — | 0.063 | 17.0 | — | — |
| 0.5 | 0.008 | 69.5 | 59.0 | +10.5 |
| 0.25 | 0.004 | 64.3 | 52.0 | +12.3 |
| 0.5 | 0.016 | 80.0 | 59.0 | +21.0 |
| 0.25 | 0.008 | 66.8 | 52.0 | +14.8 |
| 0.5 | 0.031 | 79.3 | 59.0 | +20.3 |
| 0.25 | 0.016 | 74.6 | 52.0 | +22.6 |

-continued

Control of *Pyrenophora teres*
Dosage in mg active ingredient/liter final medium

| Cyprodinil (ppm ai) [mg/L] | Pyribencarb (ppm ai) [mg/L] | Observed control in % (% $C_{obs}$) observed | Expected control in % (% $C_{exp}$) expected | Synergistic benefit in % control % $C_{obs}$ − % $C_{exp}$ difference |
|---|---|---|---|---|
| 0.5 | 0.063 | 79.2 | 65.9 | +13.3 |
| 0.25 | 0.031 | 76.9 | 52.0 | +24.9 |

b) Protective Treatment of Leaf Pieces

Barley leaf segments are placed on agar in multiwell plates (24-well format) and sprayed with test solutions. After drying, the leaf disks are inoculated with a spore suspension of the fungus. After appropriate incubation the activity of a compound is assessed 4 days after inoculation as preventive fungicidal activity. The fungicide interactions in the combinations are calculated according to the COLBY method.

Example B-3

Action Against *Pseudocercosporella herpotrichoides* var. *acuformis* (Causal Fungus of Eyespot Disease in Cereals)—Fungal Growth Assay Conidia of the fungus from cryogenic storage are directly mixed into nutrient broth (PDB potato dextrose broth). After placing a (DMSO) solution of the test compounds into a microtiter plate (96-well format) the nutrient broth containing the fungal spores is added. The test plates are incubated at 24 C and the inhibition of growth is determined photometrically after 3 days. The fungicide interactions in the combinations are calculated according to the COLBY method. The data generated in this experiment indicate synergy between cyprodinil and boscalid, cyprodinil and dodine and cyprodinil and pyribencarb when used in mixture with one another.

Control of *Pseudocercosporella herpotrichoides* var. *acuformis*
Dosage in mg active ingredient/liter final medium

| Cyprodinil (ppm ai) [mg/L] | Boscalid (ppm ai) [mg/L] | Observed control in % (% $C_{obs}$) observed | Expected control in % (% $C_{exp}$) expected | Synergistic benefit in % control % $C_{obs}$ − % $C_{exp}$ difference |
|---|---|---|---|---|
| 0.0625 | — | 23.5 | — | — |
| 0.125 | — | 40.7 | — | — |
| 0.25 | — | 28.9 | — | — |
| 0.5 | — | 19.6 | — | — |
| 1 | — | 17.5 | — | — |
| 2 | — | 24.6 | — | — |
| 4 | — | 33.6 | — | — |
| — | 0.031 | 0 | — | — |
| — | 0.063 | 2.5 | — | — |
| — | 0.125 | 32.8 | — | — |
| — | 0.25 | 58.4 | — | — |
| — | 0.5 | 77.1 | — | — |
| 4 | 0.25 | 95.3 | 72.4 | +22.9 |
| 2 | 0.125 | 91.4 | 49.4 | +42.0 |
| 1 | 0.063 | 67.6 | 19.6 | +48.0 |
| 0.5 | 0.031 | 46.7 | 19.6 | +27.1 |
| 4 | 0.5 | 95.9 | 84.8 | +11.1 |

-continued

Control of *Pseudocercosporella herpotrichoides* var. *acuformis*
Dosage in mg active ingredient/liter final medium

| Cyprodinil (ppm ai) [mg/L] | | Observed control in % (% $C_{obs}$) observed | Expected control in % (% $C_{exp}$) expected | Synergistic benefit in % control % $C_{obs}$ − % $C_{exp}$ difference |
|---|---|---|---|---|
| 2 | 0.25 | 95.2 | 68.6 | +26.6 |
| 1 | 0.125 | 88.5 | 44.6 | +43.9 |
| 0.5 | 0.063 | 68.7 | 21.6 | +47.1 |
| 0.25 | 0.031 | 45.2 | 28.9 | +16.3 |
| 2 | 0.5 | 95.9 | 82.7 | +13.2 |
| 1 | 0.25 | 93.8 | 65.7 | +28.1 |
| 0.5 | 0.125 | 86.3 | 46.0 | +40.3 |
| 0.25 | 0.063 | 65.7 | 30.7 | +35.0 |
| 1 | 0.5 | 94.8 | 81.1 | +13.7 |
| 0.5 | 0.25 | 94.8 | 66.5 | +28.3 |
| 0.25 | 0.125 | 86.6 | 52.2 | +34.4 |
| 0.125 | 0.063 | 57.1 | 42.2 | +14.9 |
| 0.0625 | 0.031 | 40.1 | 23.5 | +16.6 |
| 0.5 | 0.5 | 95.8 | 81.6 | +14.2 |
| 0.25 | 0.25 | 92.2 | 70.4 | +21.8 |
| 0.125 | 0.125 | 79.7 | 60.2 | +19.5 |
| 0.0625 | 0.063 | 66.3 | 25.4 | +40.9 |
| | Dodine (ppm ai) [mg/L] | | | |
| 0.125 | — | 10.9 | — | — |
| 0.25 | — | 14.8 | — | — |
| 0.5 | — | 13.7 | — | — |
| 1 | — | 17.9 | — | — |
| 2 | — | 20.3 | — | — |
| 4 | — | 25.9 | — | — |
| 8 | — | 33.6 | — | — |
| 16 | — | 46.2 | — | — |
| — | 0.125 | 0 | — | — |
| — | 0.25 | 0 | — | — |
| — | 0.5 | 0 | — | — |
| — | 1 | 0 | — | — |
| — | 2 | 1.4 | — | — |
| — | 4 | 31.3 | — | — |
| — | 8 | 70.5 | — | — |
| — | 16 | 72.4 | — | — |
| 8 | 4 | 71.3 | 54.4 | +16.9 |
| 4 | 2 | 46.8 | 26.9 | +19.9 |
| 2 | 1 | 23.3 | 20.3 | +3.0 |
| 1 | 0.5 | 37.0 | 17.9 | +19.1 |
| 0.5 | 0.25 | 25.7 | 13.7 | +12.0 |
| 0.25 | 0.125 | 31.2 | 14.8 | +16.4 |
| 16 | 16 | 97.2 | 85.1 | +12.1 |
| 8 | 8 | 84.8 | 80.4 | +4.4 |
| 4 | 4 | 69.1 | 49.0 | +20.1 |
| 2 | 2 | 33.8 | 21.4 | +12.4 |
| 1 | 1 | 28.3 | 17.9 | +10.4 |
| 2 | 4 | 64.3 | 45.2 | +19.1 |
| 1 | 2 | 40.2 | 19.1 | +21.1 |
| 0.5 | 1 | 30.0 | 13.7 | +16.3 |
| 0.25 | 0.5 | 21.6 | 14.8 | +6.8 |
| 0.125 | 0.25 | 33.4 | 10.9 | +22.5 |
| | Pyribencarb (ppm ai) [mg/L] | | | |
| 0.125 | — | 16.6 | — | — |
| 0.5 | — | 30.1 | — | — |
| 1 | — | 19.3 | — | — |
| 2 | — | 21.5 | — | — |
| 4 | — | 27.2 | — | — |
| — | 0.008 | 16.2 | — | — |
| — | 0.016 | 40.1 | — | — |
| — | 0.031 | 61.1 | — | — |
| 4 | 0.031 | 86.7 | 71.6 | +15.1 |
| 2 | 0.016 | 67.4 | 53.0 | +14.4 |
| 1 | 0.008 | 52.3 | 32.4 | +19.9 |
| 2 | 0.031 | 86.9 | 69.4 | +17.5 |
| 1 | 0.016 | 61.0 | 51.7 | +9.3 |
| 0.5 | 0.008 | 55.2 | 41.4 | +13.8 |
| 1 | 0.031 | 80.2 | 68.6 | +11.6 |
| 0.125 | 0.008 | 50.2 | 30.1 | +20.1 |

Example B-4

Action Against *Fusarium culmorum* (Causal Fungus of Wheat Root Rot)—Fungal Growth Assay Conidia of the fungus from cryogenic storage are directly mixed into nutrient broth (PDB potato dextrose broth). After placing a (DMSO) solution of the test compounds into a microtiter plate (96-well format) the nutrient broth containing the fungal spores is added. The test plates are incubated at 24 C and the inhibition of growth is determined photometrically after 2 days. The fungicide interactions in the combinations are calculated according to the COLBY method. The data generated in this experiment indicate synergy between cyprodinil and dodine, cyprodinil and fluazinam and cyprodinil and pyribencarb when used in mixture with one another.

Control of *Fusarium culmorum*
Dosage in mg active ingredient/liter final medium

| Cyprodinil (ppm ai) [mg/L] | | Observed control in % (% $C_{obs}$) observed | Expected control in % (% $C_{exp}$) expected | Synergistic benefit in % control % $C_{obs}$ − % $C_{exp}$ difference |
|---|---|---|---|---|
| | Dodine (ppm ai) [mg/L] | | | |
| 4 | — | 0 | — | — |
| 8 | — | 0 | — | — |
| 16 | — | 6.7 | — | — |
| 32 | — | 26.9 | — | — |
| — | 8 | 3.3 | — | — |
| — | 16 | 15.1 | — | — |
| 32 | 16 | 98.0 | 38.0 | +60.0 |
| 16 | 8 | 96.3 | 9.8 | +86.5 |
| 16 | 16 | 98.0 | 20.8 | +77.2 |
| 8 | 8 | 80.8 | 3.3 | +77.5 |
| 8 | 16 | 98.0 | 15.1 | +82.9 |
| 4 | 8 | 46.3 | 3.3 | +43.0 |
| 4 | 16 | 97.6 | 15.1 | +82.5 |
| | Fluazinam (ppm ai) [mg/L] | | | |
| 2 | — | 0 | — | — |
| 4 | — | 0 | — | — |
| 8 | — | 0 | — | — |
| 16 | — | 9.8 | — | — |
| 32 | — | 16.4 | — | — |
| — | 0.063 | 5.1 | — | — |
| — | 0.125 | 11.8 | — | — |
| — | 0.25 | 27.4 | — | — |
| — | 0.5 | 35.7 | — | — |
| — | 1 | 72.4 | — | — |

-continued

| Control of *Fusarium culmorum* Dosage in mg active ingredient/liter final medium | | | | |
|---|---|---|---|---|
| Cyprodinil (ppm ai) [mg/L] | | Observed control in % (% $C_{obs}$) observed | Expected control in % (% $C_{exp}$) expected | Synergistic benefit in % control % $C_{obs}$ − % $C_{exp}$ difference |
| 32 | 0.25 | 96.0 | 39.3 | +56.7 |
| 32 | 0.5 | 97.7 | 46.2 | +51.5 |
| 16 | 0.25 | 83.4 | 34.5 | +48.9 |
| 8 | 0.125 | 17.3 | 11.8 | +5.5 |
| 4 | 0.063 | 19.5 | 5.1 | +14.4 |
| 32 | 1 | 97.9 | 77.0 | +20.9 |
| 16 | 0.5 | 96.2 | 42.0 | +54.2 |
| 8 | 0.25 | 36.6 | 27.4 | +9.2 |
| 4 | 0.125 | 20.1 | 11.8 | +8.3 |
| 2 | 0.063 | 21.5 | 5.1 | +16.4 |
| 16 | 1 | 96.4 | 75.1 | +21.3 |
| 8 | 0.5 | 74.3 | 35.7 | +38.6 |
| 8 | 1 | 96.9 | 72.4 | +24.5 |
| 4 | 0.5 | 63.6 | 35.7 | +27.9 |
| | Pyribencarb (ppm ai) [mg/L] | | | |
| 8 | — | 2.4 | — | — |
| 16 | — | 8.4 | — | — |
| 32 | — | 21.7 | — | — |
| — | 0.125 | 0 | — | — |
| — | 0.25 | 8.7 | — | — |
| — | 0.5 | 11.5 | — | — |
| — | 1 | 16.2 | — | — |
| 32 | 0.25 | 75.2 | 28.5 | +46.7 |
| 16 | 0.125 | 19.9 | 8.4 | +11.5 |
| 32 | 0.5 | 85.3 | 30.7 | +54.6 |
| 16 | 0.25 | 37.4 | 16.4 | +21.0 |
| 32 | 1 | 88.4 | 34.4 | +54.0 |
| 16 | 0.5 | 49.3 | 18.9 | +30.4 |
| 8 | 0.25 | 23.8 | 10.9 | +12.9 |
| 16 | 1 | 55.3 | 23.3 | +32.0 |
| 8 | 0.5 | 26.0 | 13.6 | +12.4 |
| 8 | 1 | 31.4 | 18.2 | +13.2 |

The combinations according to the invention exhibit good activity in all of the above examples.

What is claimed is:

1. A method of controlling phytopathogenic diseases on useful plants or on propagation material thereof, which comprises applying to the useful plants, the locus thereof or propagation material thereof a composition that, in addition to customary inert formulation adjuvants, comprises, as active ingredients, synergistically effective amounts of component (A) and component (B), wherein component (A) is Cyprodinil and component (B) is Fluazinam; wherein the step of applying comprises applying Cyprodinil at a rate of 5 to 2000 g a.i./ha and Fluazinam at a rate of 1 to 5000 g a.i./ha, and the Cyprodinil and Fluazinam are present at a weight ratio of component (A) to component (B) is from 100:1 to 1:100.

2. A method of controlling phytopathogenic diseases on useful plants, which comprises applying to the useful plants or the locus thereof a composition that, in addition to customary inert formulation adjuvants, comprises, as active ingredients, synergistically effective amounts of component (A) and component (B), wherein component (A) is Cyprodinil and component (B) is Fluazinam, wherein the step of applying comprises applying Cyprodinil at a rate of 5 to 2000 g a.i./ha and Fluazinam at a rate of 1 to 5000 g a.i./ha, and the Cyprodinil and Fluazinam are present at a weight ratio of component (A) to component (B) is from 100:1 to 1:100.

3. A method according to claim 2, wherein the useful plants are cereal plants.

4. A method according to claim 2, wherein the useful plants are fruit plants or vegetable plants.

5. A method according to claim 2, wherein the useful plants are grape plants.

6. A method according to claim 1, wherein the weight ratio of component (A) to component (B) is from 20:1 and 1:50.

7. A method according to claim 3, wherein the useful plants are wheat plants.

8. A method according to claim 1, wherein the step of applying comprises applying from 20 to 4000 g of the composition per hectare.

9. A method according to claim 1, wherein the phytopathogenic disease is caused by *Fusarium*.

10. A method according to claim 2, wherein the phytopathogenic disease is caused by *Fusarium*.

* * * * *